United States Patent [19]

Helting

[11] 4,029,766
[45] June 14, 1977

[54] PROTECTIVE ANTIGEN FROM PERTUSSIS, PROCESS FOR ITS PREPARATION AND PRODUCTS CONTAINING THIS ANTIGEN

[75] Inventor: Torsten Bertil Helting, Marbach-Marburg an der Lahn, Germany

[73] Assignee: Behringwerke Aktiengesellschaft, Marburg an der Lahn, Germany

[22] Filed: Dec. 22, 1975

[21] Appl. No.: 643,123

[30] Foreign Application Priority Data

Dec. 24, 1977 Germany ............................ 2461439

[52] U.S. Cl. .............................. 424/92; 260/112 R
[51] Int. Cl.² ........................................ A61K 39/02
[58] Field of Search .................. 260/112 R; 424/92

[56] References Cited

UNITED STATES PATENTS

| | | | |
|---|---|---|---|
| 3,395,219 | 7/1968 | Millman | 424/92 |
| 3,405,218 | 10/1968 | Haskell et al. | 424/92 |
| 3,465,078 | 9/1969 | Spiesel | 424/92 |

OTHER PUBLICATIONS

Azuma et al: Chemical Abstracts, vol. 78, 39687q, (1973).
Greene et al: Chemical Abstracts, vol. 82, 12575x, (1975).

*Primary Examiner*—Dolph H. Torrence
*Attorney, Agent, or Firm*—Curtis, Morris & Safford

[57] ABSTRACT

The present invention provides a protective antigen from Bordetella pertussis, a process for its preparation by extraction of the pathogens and furthermore products, especially pertussis vaccines, which contain this antigen.

15 Claims, No Drawings ns has
PROTECTIVE ANTIGEN FROM PERTUSSIS, PROCESS FOR ITS PREPARATION AND PRODUCTS CONTAINING THIS ANTIGEN The present invention provides a protective antigen from Bordetella pertussis, a process for its preparation by extraction of the pathogens and subsequent adsorption of the extracted antigens on a carrier material, and furthermore products, especially pertussis vaccines, which contain this antigen.

The conventional pertussis vaccines for active immunization against the whooping-cough generally contain dead pathogens of Bordetella pertussis. It is known that these pathogens often cause local pain and inflammation of the place of vaccination, sometimes also fever and in certain cases even neurological complications such as the dreaded encephalitis.

Attempts have therefore been made to replace the pathogen containing vaccine by an extract vaccine in order to attain a better tolerance. Although the preparation of extracts from pertussis pathogens by means of salt solutions, as described several times in the literature, results in a solubilization of a small part of the protective antigen complex, the yields are relatively poor, and the extracts, as do the pathogens, consist of numerous components being toxic in part, so that they do not bring about an improved tolerance of the vaccine.

Because of the polydispersity of the antigen material, a strict limit is set to a further purification of the salt extracts. Generally, by means of the usual biochemical purification processes, a distribution of the protective activity into several fractions is obtained without substantially increasing the specific protective activity. In order to increase the yield, attempts have also been made to open the pertussis pathogens, for example by means of ultrasonics. Apart from the great apparatus expenditure, this process is not satisfactory because it does not solve the problem of attaining a higher purification degree of the protective antigen.

It should be mentioned in this connection that the so-called histamine-sensitizing factor of the pertussis pathogens may be obtained by treatment with an aqueous sodium chloride solution containing 4 M urea, and that it was not possible to remove the urea without loss of histamine-sensitizing activity. The question whether the histamine-sensitizing activity is entirely or partially identical with the protective antigen is still in dispute. Besides hints to the fact that they are different components, Y. Sato, Symp. Series Immunobiol. Standard., Vol. 13, pp. 214 – 220, indicates that the treatment of a 22 S pertussis antigen with urea destroys the protective activity.

It is therefore the object of the present invention to provide a protective antigen complex in soluble form from pertussis pathogens with higher yields and optionally higher purification degree than hitherto attained, and to use the purified antigen as the substantially active component of pertussis vaccines.

This and other objects are accomplished by the process of this invention the, essence of which comprises treating pertussis pathogens with solutions of denaturing agents, separating the pathogens and adsorbing the solubilized material either directly or after a further purification in a denaturing medium on a carrier material insoluble in water.

Subject of the present invention is therefore a process for the preparation of a protective antigen from Bordetella pertussis, which comprises mixing pathogens of Bordetella pertussis with an aqueous solution of a denaturing agent and a neutral salt, separating the liquid supernatant from the residue of the pathogens, adding a water-insoluble adsorption agent, optionally in the presence of the denaturing agent, and separating subsequently the denaturing agent from the aqueous suspension of the protective antigen.

The treatment of the pertussis pathogens with the cited aqueous solution, which results in an extraction of the pathogens, is carried out most easily by keeping the pathogens suspended in the solution as homogeneously as possible. However, this mode of operation involves very long extraction times. The efficiency of the extraction is increased already by slightly moving the pathogens, for example by simple stirring. Apparatus usual for homogenization may be advantageously employed in order to increase the yield and to shorten the extraction time. Depending on the agitation means, the extraction time is in a range of from ½ to 48 hours; on the average, it is about 18 hours.

The extraction temperature is advantageously from 1° to 40° C. Temperatures below room temperature, for example in a range of from 1° to 10° C, are preferred.

During the extraction, the mixture is maintained at a pH of from 6 to 10, preferably at pH 8. In the case where this pH does not establish itself, it may be adjusted by adding suitable buffer solutions.

Extract and pathogen residue are advantageously separated by centrifugation. Suitable for obtaining a cell-free extract are also filtration devices which are capable of retaining microorganisms.

Surprisingly, it has been observed that the protective antigen in a solution containing denaturing agents has the properties of a relatively homogeneous, uniform substance, so that its further purification in the presence of the denaturing agent is possible. This may be advantageously carried out by gel chromatography, by which a separation of toxic components from the protective antigen is obtained in the case where the development is obtained by means of a buffer containing a denaturing agent. Suitable media for gel chromatography are above all dextran cross-linked with epichlorohydrin, available on the market as Sephadex$^{(R)}$ of the company Pharmacia, Uppsala, Sweden, or copolymers of acrylamide and methylene-bisacrylamide, available on the market as Bio-Gel P$^{(R)}$ of the company Bio-Rad Laboratories, Richmond, U.S.A.

As buffer substances to be used in the process of the invention, compounds normally used in biochemical work for stabilizing the pH of the solution may be employed, advantageously those described in Handbook of Biochemistry, Cleveland (Ohio), 2nd Edition, p. J 238, for example tris-(hydroxymethyl)-aminomethane. It is proved to be advantageous to add small amounts (from about 1 to 20 mM) of so-called chelate or complex forming agent to the buffer solution, for example ethylene-diamine- tetraacetate (EDTA).

When an adsorbent is used, its choice depends substantially on the intended use of the protective antigen. For the preferred use in a pertussis vaccine, an immunological additive proved in vaccine manufacture is preferably used which may be of inorganic origin, such as calcium phosphate or aluminum oxide. Preferably, $AlPO_4$ and/or $C\gamma$-aluminum hydroxide are employed in a final concentration (solids concentration in the final product) of from 0.05 to 0.4% (w/v). However, also organic polymers are suitable, especially polyanionic additives insoluble in the solutions of the denaturing agents, for example derivatives of polyacrylic acid. When the antigen is not to be administered to humans and animals, any adsorbent usual for the adsorption of proteins may be added to the solution of the protective antigen.

The denaturing agent is advantageously removed by dialysis. Since the protective antigen in the physiological medium cannot pass through the dialysis membrane, in contrast to the denaturing agent, the progressive discharge of the latter cause precipitation of the protective antigen on the adsorbent, if such is present.

In the case where a sterile product is required, the work-up, from the extraction to the obtention of the final, optionally adsorbed, material, may be carried out under sterile conditions. Alternatively, before removing the denaturing agent and optionally before adding the adsorbent, a sterilization filtration is intercalated, and the subsequent work-up has to be done under sterile conditions.

By denaturing agents, in accordance with this invention, are to be understood chemical compounds which cause dissociation of protein molecules into subunits, especially by splitting hydrogen bonds. Suitable compounds are urea or guanidine or the salts thereof, especially guanidine hydrochloride. The denaturing agents are used in concentrations of from 2 to 6 mols/liter, preferably from 4 to 6 mols/l, relative to the total solution.

Preferred neutral salts are water-soluble alkali metal halides, for example NaCl or KCl, and they are used in a concentration of from 0.5 to 4 mols/l, preferably 1 mol/l, relative to the total solution. Denaturing agent and neutral salt have a synergistic effect in the extraction of the protective antigen.

Suitable starting materials for the process of the invention are Bordetella pertussis pathogens. They are propagated in known manner, for example by growing them in Cohen-Wheeler nutrient solution at about 35° C with agitation, and they are obtained by precipitation with acids or organic solvents, or by centrifugation. For example, the Bordetella pertussis fermentation culture is subjected to an acid precipitation at pH 3 – 5, preferably pH 4. For the acid precipitation, all mineral acids, preferably 1 N hydrochloric acid, are appropriate, furthermore organic acids, for example acetic acid. Pathogens separated from the culture medium by centrifugation are of the same quality as those obtained by means of acetone or acid precipitation. The pathogens are advantageously used in aqueous suspension in a concentration of from 50 ($10^9$) to 1000 ($10^9$), preferably from 100 ($10^9$) to 400 ($10^9$), per ml.

The potency of pertussis vaccines is tested in animal tests according to Kendrick (P.L. Kendrick et al., Amer. J. Publ. Health 37, 803 (1947) and Fed. Reg. 33, No. 118, 8818, Paragraph 73.404 (1968)). Groups of 18 mice each are immunized with the pertussis antigen in three different states of dilution and, after 13 days, the immunity is tested by an intracerebral injection-infection with 200 $LD_{50}$ of living pathogens of Bordetella pertussis. A standard vaccine of known protective value is always tested in the same manner. The protective unit value which results from these tests is a guideline for the protective activity in humans (see Medical Res. Council Brit. Med. J. No. 5128, 994 (1959)).

After the extraction of pertussis pathogen suspensions having a pathogen density of 100 ($10^9$) pathogens per ml according to the conditions of the process of this invention, values of from 25 to 75 IU/ml have been found. A vaccine having at least 8 IU/ml is generally acknowledged as being a potent vaccine.

The toxicity is determined according to the rules of U.S. Department of Health, Education and Welfare in the following manner: 10 mice are treated with 0.5 ml of the pertussis vaccine to be examined in a 1:2 dilution ratio. According to the National Institute of Health (NIH) Standards published in Federal Reg. 33, No. 118,8818 (1968), Paragraph 73.403, weight gains of 3 g/7 days are required. In the case of a pertussis antigen prepared according to this invention, the average weight gain of the mice is from 1 to 3 g after 72 hours, and from 5 to 6 g after 7 days. The antigen therefore does not contain any toxic parts of the pertussis pathogens and is well tolerated.

In addition to the disclosed process for the preparation of the protective antigen from pertussis, the present invention provides protective antigens the parameters of which result from their preparation according to the above process.

The present invention provides furthermore products containing the protective antigen from pertussis in accordance with this invention, especially pertussis vaccines for the prophylaxis of whooping-cough, or for the manufacture of pertussis antisera to be used for therapeutic or diagnostic purposes, but also diagnostic products containing the protective antigen from pertussis or antisera obtained therefrom. The pertussis vaccines to be manufactured in accordance with this invention are suitable for parenteral and oral administration.

The solution or suspension of the antigen may be protected by adding antimicrobial preservation agents such as sodium timerfonate. In order to obtain a polyvalent vaccine, the pertussis antigen may be mixed in usual manner with other antigens and/or toxoids.

The present invention represents a substantial progress in the obtention of protective pertussis antigens or pertussis vaccines. The process is simple, and the protective activity of the adsorbed extract antigen is surprisingly high as compared with the data known from the literature. The high yield in the extract is illustrated by the fact that pathogens having been subjected to a 6 M urea extraction lost 80% and more of their protective activity. In the case of pathogens extracted by means of salt, however, a loss of only 10 – 20% of the protective activity is found after separation of the extract. The fact that the antigen extract is not substantially polydispersible in a denaturing medium allows separation of toxic components. Thus, an important increase in tolerance is to be expected when the antigen is administered to human beings, especially children.

The following examples illustrate the invention.

EXAMPLE 1:

6 liters of 1 M tris-(hydroxymethyl)-aminomethane-HCl buffer having a pH of 8.0 and containing 50 mM of EDTA are added to 40 liters of a pertussis pathogen suspension having a density of 100 ($10^9$) pathogens per ml. After mixing, 14.4 kg of urea and 3.48 kg of NaCl are added, a volume of 60 l is obtained by adding water, and the suspension is stirred overnight by means of a magnetic agitator. After elimination of the pathogens by centrifugation (Sharpless concurrent centrifuge), 3 liters of 2% suspension of $AlPO_4$ in admixture with a suspension of 1% $Al(OH)_3$ is added. Subsequently, the urea is eliminated by dialysis against sterile 0.15 M NaCl in a Hollow-Fiber apparatus of Messrs. Amicon. After settling of the adsobate, the total volume is adjusted to 40 l by means of isotonic sodium chloride solution. An immunogen so obtained yielded 25 IU/ml in the protection test according to Kendrick.

An extract prepared from the same starting material by treatment of the pathogens with 0.5 M NaCl yielded only 4.5 IU/ml in the protection test according to Kendrick.

Toxicity determined in mice: 3 days + 3.2 g; 7 days + 5.8 g.

EXAMPLE 2

After an extraction process according to Example 1, but starting with 200 $(10^9)$ pathogens per ml and an aqueous solution of 6 M guanidine-hydrochloride + 1 M NaCl, the protective value of the extract was 76 IU/ml.

Toxicity determined in mice: 3 days + 1.0 g; 7 days + 5.2 g.

EXAMPLE 3

The extract obtained according to Example 1, but with the use of 9.6 kg of urea instead of 14.4 kg, is concentrated to 2 l by means of an ultrafilter and introduced into a column of Sephadex$^{(R)}$ G-150, equilibrated with the extraction buffer (containing 4 M urea). Before chromatography, the concentrated extract, at a volume equivalent to 80 $(10^9)$ pathogens per ml, yielded 8.25 IU/ml corresponding to 130 IU/mg of protein. The material, corresponding to the exclusion volume of the column up to a molecular weight of about 90,000, is pooled, and the urea is eliminated by dialysis against 0.15 M sodium chloride solution. The fraction obtained after chromatography was concentrated to a volume corresponding to a density of 360($10^9$) pathogens per ml and yielded 84.5 IU/ml in the protection test, corresponding to 525 IU/mg of protein.

What is claimed is:

1. A method for making a protective antigen from *Bordetella pertussis*, which method comprises mixing pathogens of *Bordetella pertussis* with an aqueous solution of a denaturing agent and a netural salt, separating the liquid supernatant, which contains the protective antigen suspended therein, from the residue of the pathogens, and subsequently separating the denaturing agent from the aqueous suspension of the protective antigen.

2. A method as in claim 1 wherein a water-insoluble adsorbent is added to said liquid supernatant before separating the denaturing agent.

3. A method as in claim 1, wherein said pathogens are present in a concentration of from 50($10^9$)/ml to 1000($10^9$)/ml.

4. A method as in claim 1 wherein said denaturing agent is urea, guanidine, or a guanidine or urea salt.

5. A method as in claim 1 wherein the liquid supernatant is purified in the presence of the denaturing agent and a water-insoluble adsorbent is subsequently added thereto.

6. A method as in claim 1 wherein said denaturing agent is present in a concentration from 2 mols/1 to 6 mols/1.

7. A method as in claim 1 wherein said neutral salt is at least one member selected from the group consisting of sodium chloride and potassium chloride.

8. A method as in claim 1 wherein said neutral salt is present in a concentration from 0.5 mol/1 to 4 mols/1.

9. A method as in claim 1 wherein the pH is from 6 to 10.

10. A method as in claim 1 wherein the temperature is from 1° to 40° C.

11. A method as in claim 1 wherein said water-insoluble adsorbent is at least one member selected from the group consisting of $AlPO_4$ and Cγ-aluminum hydroxide and is present in a concentration from 0.05 to 0.2%.

12. A protective antigen prepared by the method of claim 1.

13. A pertussis vaccine containing the protective antigen of claim 12.

14. A product containing the protective antigen of claim 12.

15. A method for making a protective antigen from *Bordetella pertussis*, which method comprises mixing pathogens of *Bordetella pertussis*, at a temperature between 1° C. and 40° C., with an aqueous solution of (1) a denaturing agent which is urea, guanidine, or a urea or guanidine salt and (2) a water-soluble alkali chloride, the concentration of said pathogens being from 50($10^9$)/ml to 1000 ($10^9$)/ml, the concentration of said denaturing agent being from 2 mols/1 to 6 mols/1, the concentration of said alkali chloride being from 0.5 mol/1 to4 mols/1, and the pH being from 6 to 10, separating the liquid supernatant, which contains the protective antigen suspended therein, from the residue of the pathogens, and subsequently separating the denaturing agent from the aqueous suspension of the antigen.

* * * * *

UNITED STATES PATENT AND TRADEMARK OFFICE
CERTIFICATE OF CORRECTION

PATENT NO. : 4,029,766
DATED : June 14, 1977
INVENTOR(S) : Helting

It is certified that error appears in the above-identified patent and that said Letters Patent are hereby corrected as shown below:

In the Heading, Item [30], change "Dec. 24, 1977" to

--Dec. 24, 1974--.

Signed and Sealed this

Fifteenth Day of November 1977

[SEAL]

Attest:

RUTH C. MASON
Attesting Officer

LUTRELLE F. PARKER
Acting Commissioner of Patents and Trademarks